(12) United States Patent
Endo et al.

(10) Patent No.: US 7,078,212 B1
(45) Date of Patent: Jul. 18, 2006

(54) MUTANT α-AMYLASES

(75) Inventors: Keiji Endo, Tochigi (JP); Kazuaki Igarashi, Tochigi (JP); Yasuhiro Hayashi, Tochigi (JP); Hiroshi Hagihara, Tochigi (JP); Katsuya Ozaki, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/590,375

(22) Filed: Jun. 9, 2000

(30) Foreign Application Priority Data

Jun. 10, 1999 (JP) .............................. 1999-163569

(51) Int. Cl.
*C12N 9/26* (2006.01)
*C12N 9/28* (2006.01)
*C07H 21/04* (2006.01)

(52) U.S. Cl. ...................... 435/201; 435/202; 536/23.2

(58) Field of Classification Search ................ 435/202, 435/201; 510/226; 536/23.2
See application file for complete search history.

(56) References Cited

U.S. PATENT DOCUMENTS 5,736,499 A * 4/1998 Mitchinson et al. ........ 510/392
6,197,565 B1 * 3/2001 Svendsen et al. ........... 435/202

FOREIGN PATENT DOCUMENTS

WO  9923211 A1  5/1999

OTHER PUBLICATIONS

Declerck et al. (Oct. 1995) Protein Engineering, vol. 8 (10), pp. 1029-1037 (abstract).*
David J. Lipman et al., Science, Mar. 22, 1985, pp. 1435-1441.
Yutaka Suzuki et al., The Journal of Biological Chemistry, vol. 264, No. 32, 1989, pp. 18933-18938.
Nathalie Declerck et al., The Journal of Biological Chemistry, vol. 265, No. 26, 1990, pp. 15481-15488.
Birgit Conrad et al., Eur. J. Biochem., vol. 230, 1995, pp. 481-490.
Kazuaki Igarashi et al., Biochemical and Biophysical Research Communications, vol. 248, 1998, pp. 372-377.

* cited by examiner

*Primary Examiner*—Elizabeth Slobodyansky
(74) *Attorney, Agent, or Firm*—Birch Stewart Kolasch & Birch LLP

(57) ABSTRACT

The invention relates to a mutant α-amylase obtained by making replacement or deletion of at least one of amino acid residues such as the 167th Gln, 169th Tyr and 178th Ala in the amino acid sequence set forth in SEQ ID NO:1 in an α-amylase having said amino acid sequence, or an α-amylase having a homology of at least 70% to said amino acid sequence, a gene encoding the mutant α-amylase, a vector, transformed cells, a process for producing a mutant α-amylase, comprising culturing the transformed cells, and a detergent composition comprising the mutant α-amylase.

The mutant α-amylase of the invention has excellent properties of high resistance to chelating agents, high specific activity in an alkaline region and excellent stability to heat, and is hence useful for detergents for automatic dish washer, laundry detergents and the like.

20 Claims, 3 Drawing Sheets

MUTANT α-AMYLASES

BACKGROUND OF THE INVENTION

1. Field of the Invention

The present invention relates to mutant liquefying alkaline α-amylases which have excellent heat resistance, and are particularly useful as enzymes for detergents, and genes thereof.

2. Description of the Background Art

When an α-amylase [EC.3.2.1.1] is used as an enzyme for detergents, it has heretofore been said that a liquefying alkaline α-amylase, which can decompose starch at random and is stable to alkali and also to both chelating component and oxidation bleaching component, is preferred. However, in liquefying amylases, a calcium ion is generally important for maintaining the structure of the enzymes, and the stability thereof is lowered in the presence of a chelating agent. Besides, most of such enzymes have had the optimum pH in a neutral to weakly acidic range.

Under the foregoing circumstances, the present inventors found that enzymes produced by *alkaliphilic Bacillus* sp. KSM-K38 (FERM BP-6946) and *Bacillus* sp. KSM-K36 (FERM BP-6945) strains isolated from soil do not show the lowering of activity at all in the presence of a chelating agent at a high concentration by which deactivation is recognized in the conventional liquefying α-amylases, and have resistance to surfactants and oxidizing agents and that they have higher activity on the alkaline side compared with the conventional liquefying α-amylases and are useful as enzymes for detergents (Japanese Patent Application No. 362487/1998.

However, said enzymes exhibit inactivation at a temperature of 50° C. or higher, and so the heat resistance thereof have been somewhat insufficient in view of the fact that cleaning of clothing and tableware is generally conducted at about 10 to 60° C.

SUMMARY OF THE INVENTION

It is an object of the present invention to provide an α-amylase which is a liquefying alkaline α-amylase that has high activity on the alkaline side and is stable to both chelating component and oxidation bleaching component, and has excellent heat resistance.

The present inventors have acquired various mutant enzymes as to liquefying alkaline α-amylases and investigated them. As a result, it has been found that when a mutation is introduced into a specified amino acid residue in the amino acid sequence (SEQ ID NO:1) of amylase derived from KSM-K38, the heat resistance of the enzyme is improved without losing its properties such as resistance to chelating agents and resistance to oxidizing agents and high specific activity in an alkaline region, and that the heat resistance can be further improved by combining such mutations.

According to the present invention, there is thus provided a mutant α-amylase obtained by making replacement or deletion of at least one residue of amino acid residues respectively corresponding to the 11th Tyr, 16th Glu, 49th Asn, 84th Glu, 144th Ser, 167th Gln, 169th Tyr, 178th Ala, 188th Glu, 190th Asn, 205th His and 209th Gln in the amino acid sequence set forth in SEQ ID NO:1 in an α-amylase having said amino acid sequence, or an α-amylase having a homology of at least 70% to said amino acid sequence.

According to the present invention, there is also provided a mutant α-amylase obtained by making replacement of a sequence corresponding to 11 to 100 amino acid residues from the amino terminal in the amino acid sequence set forth in SEQ ID NO:1 in an α-amylase having said amino acid sequence, or an α-amylase having a homology of at least 70% to said amino acid sequence by an amino acid sequence of another liquefying α-amylase corresponding to said sequence of the amino acid residues.

According to the present invention, there are further provided genes respectively encoding these mutant α-amylases, vectors having each of the genes, cells transformed by such a vector, and a production process of these mutant α-amylases, comprising culturing the transformed cells.

According to the present invention, there is still further provided a detergent composition comprising any one of these mutant α-amylases.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

Figure 1:
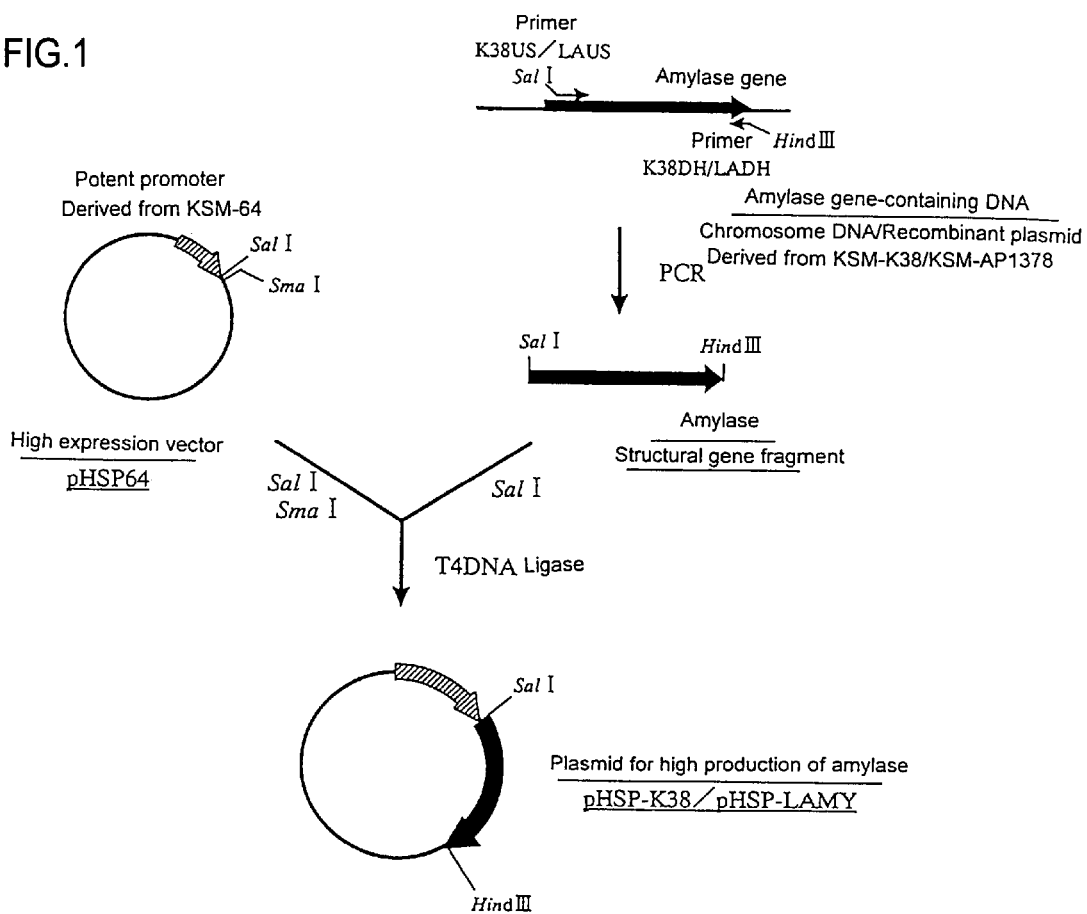
FIG. 1 illustrates a method for preparing a recombinant plasmid for the production of α-amylases derived from KSM-K38 and KSM-AP1378 strains.

The mutant α-amylases according to the present invention are obtained by mutating a gene encoding a liquefying alkaline α-amylase having the amino acid sequence set forth in SEQ ID NO:1 or an amino acid sequence having a homology of at least 70% to said amino acid sequence. However, an example where heat resistance is improved by deletion and/or replacement of an amino acid has also been conducted on the conventional liquefying α-amylases. For example, an enzyme obtained by deleting residues from the 177th Arg to the 178th Gly in an enzyme derived from *B. amyloliquefaciens* (J. Biol. Chem., 264, 18933, 1989) and an enzyme obtained by replacing the 133rd His in an enzyme derived from *B. licheniformis* by Tyr (J. Biol. Chem., 265, 15481, 1990) have been reported. However, the liquefying alkaline α-amylases used in the present invention have a low degree of amino acid homology with the conventional liquefying alkaline α-amylases. In these α-amylases, a site corresponding to the residues from the 177th Arg to the 178th Gly has been already deleted, and the amino acid corresponding to the 133rd His has been already Tyr. Therefore, the examples of the conventional enzymes cannot be always applied. More specifically, the mutations of the amino acid sequence for improving the heat resistance in the present invention are entirely different from the examples up to the date.

Examples of the liquefying alkaline α-amylases include an enzyme (Japanese Patent Application No. 362487/1998) derived from a *Bacillus* sp. KSM-K38 (FERM BP-6946) strain separated from soil by the present inventors and having the amino acid sequence of SEQ ID NO:1 and an enzyme (SEQ ID NO:4) (Japanese Patent Application No. 362487/1998) derived from *Bacillus* sp. KSM-K36 (FERM BP-6945) and having a homology of about 95% to the amino acid sequence of SEQ ID NO:1. Incidentally, the homology of the amino acid sequence is calculated in accordance with the Lipman-Pearson method (Science, 227, 1435, 1985).

In order to obtain the mutant α-amylase according to the present invention, a gene encoding a liquefying α-amylase is first cloned from microorganisms which produce said liquefying α-amylase. As a method therefor, a general gene recombination method may be used. For example, the method described in Japanese Patent Application Laid-Open No. 336392/1996 may be used. Examples of the gene include those set forth in SEQ ID NO:3 and SEQ ID NO:5.

A mutation is then introduced into the gene thus obtained. As a method therefor, any method may be adopted so far as it is a method of site-specific mutation commonly performed. The mutation can be performed, for example, by using a Site-Directed Mutagenesis System Mutan-Super Express Km kit produced by Takara Shuzo Co., Ltd. An optional sequence of the gene may be replaced by a sequence of another gene corresponding to the optional sequence by using the recombinant PCR (polymer chain reaction) method (PCR protocols, Academic Press, New York, 1990).

The mutation for improving the heat resistance in the present invention is desirably a mutation in which an amino acid residue corresponding to the 11th Tyr in the amino acid sequence set forth in SEQ ID NO:1 is replaced by Phe, an amino acid residue corresponding to the 16th Glu by Pro, an amino acid residue corresponding to the 49th Asn by Ser, an amino acid residue corresponding to the 84th Glu by Gln, an amino acid residue corresponding to the 144th Ser by Pro, an amino acid residue corresponding to the 167th Gln by Glu, an amino acid residue corresponding to the 169th Tyr by Lys, an amino acid residue corresponding to the 178th Ala by Gln, an amino acid residue corresponding to the 188th Glu by Asp, an amino acid residue corresponding to the 190th Asn by Phe, an amino acid residue corresponding to the 205th His by Arg, or an amino acid residue corresponding to the 209th Gln by Val.

The improvement of heat resistance can also be achieved by replacing an amino acid sequence corresponding to 11 to 100 amino acid residues from the amino terminal (Asp) in the amino acid sequence of SEQ ID NO:1 according to the present invention, preferably a sequence corresponding to amino acid residues from the 1st Asp to the 19th Gly, by an amino acid sequence of another liquefying α-amylase corresponding to said sequence of the amino acid residues.

Examples of said another liquefying α-amylase used in the replacement include an enzyme having the amino acid sequence set forth in SEQ ID NO:2. A site of its amino acid sequence corresponding to said amino acid residues from the 1st Asp to the 19th Gly is from the 1st His to the 21st Gly. The enzyme is an liquefied α-amylase derived from a *Bacillus* sp. KSM-AP1378 (FERM BP-3048) strain, and the sequence of the gene is disclosed in Japanese Patent Application Laid-Open No. 336392/1996.

In the mutant α-amylases according to the present invention, a mutation with at least two kinds of replacement or deletion selected from the replacement or deletion of the above-described various kinds of amino acid residues and the replacement of the amino acid sequences combined with each other is also effective, and mutant enzymes more improved in heat resistance can be obtained by such a combination. More specifically, examples of the combination of mutations include a combination of at least two of the replacement or deletion of the various kinds of amino acid residues, a combination of at least two of the replacement of the amino acid sequence, and a combination of at least two of the replacement or deletion of the amino acid residues and the replacement of the amino acid sequence. Preferably, at least two mutations may be suitably combined from among mutations in which an amino acid residue corresponding to the 49th Asn is replaced by Ser, an amino acid residue corresponding to the 167th Gln by Glu, an amino acid residue corresponding to the 169th Tyr by Lys, an amino acid residue corresponding to the 190th Asn by Phe, an amino acid residue corresponding to the 205th His by Arg, and an amino acid residue corresponding to the 209th Gln by Val, and a mutation in which an amino acid sequence corresponding to amino acid residues from the 1st Asp to the 19th Gly is replaced by an amino acid sequence from the 1st His to the 21st Gly in the amino acid sequence set forth in SEQ ID NO:2.

Examples of the most preferred combination include a combination of mutations in which an amino acid residue corresponding to the 49th Asn is replaced by Ser, an amino acid residue corresponding to the 167th Gln by Glu, an amino acid residue corresponding to the 169th Tyr by Lys, an amino acid residue corresponding to the 190th Asn by Phe, an amino acid residue corresponding to the 205th His by Arg, and an amino acid residue corresponding to the 209th Gln by Val, and a combination of a mutation in which an amino acid sequence corresponding to amino acid residues from the 1st Asp to the 19th Gly is replaced by an amino acid sequence from the 1st His to the 21st Gly in the amino acid sequence set forth in SEQ ID NO:2 with a mutation in which an amino acid residue corresponding to the an amino acid residue corresponding to the 167th Gln by Glu, an amino acid residue corresponding to the 190th Asn by Phe, or an amino acid residue corresponding to the 209th Gln by Val.

In addition, mutations for improving other properties than the heat resistance, for example, a mutation for more enhancing resistance to oxidizing agents, in which an amino acid residue corresponding to the 107th Met is replaced by Leu, a mutation for enhancing the detergency of a laundry detergent, in which an amino acid residue corresponding to the 188th Glu is replaced by Ile, and/or the like may be combined with the above-described mutations.

The thus-obtained mutant α-amylases according to the present invention are improved in stability to heat without losing excellent properties of high resistance to chelating agents, and high specific activity in an alkaline region, and are hence useful for detergents for automatic dish washer, laundry detergents and desizing agents for fibers.

Such detergents may comprise one or more enzymes selected from debranching enzymes (for example, pullulanase, isoamylase, neopullulanase, etc.), α-glycosidases, glucoamylases, proteases, cellulases, lipases, pectinases, protopectinases, pectic acid lyases, peroxidases, laccases and catalases in addition to the above-described mutant α-amylases.

Further, surfactants such as anionic surfactants, amphoteric surfactants, nonionic surfactants and cationic surfactants, chelating agents, alkalizing agents, inorganic salts, resoiling preventives, chlorine scavengers, reducing agents, bleaching agents, fluorescent dye solubilizers, perfume bases, caking preventives, enzyme activators, antioxidants, preservatives, coloring matter, bluing agents, bleaching activators, enzyme stabilizers, phase adjusters, etc., which are commonly incorporated into the classical detergents, may be incorporated.

The detergent composition according to the present invention can be produced by combining the above-described mutant α-amylases with the publicly known detergent components described above in accordance with a method known per se in the art. The form of the detergent composition may be suitably selected as necessary for the end application intended, and the detergent composition may be provided in the form of, for example, liquid, powder or granules. The detergent composition according to the present invention can be used as a laundry detergent, bleaching detergent, detergent for automatic dish washer, drain cleaner, artificial tooth cleaner or the like. In particular, it can preferably used as a laundry detergent, bleaching detergent or detergent for automatic dish washer.

The mutant α-amylases according to the present invention may be used as compositions for liquefaction and saccharification of starch and be also caused to act on starch together with one or more enzymes selected from glucoamylase, maltase, pullulanase, isoamylase, neopullulanase, etc.

The mutant α-amylases according to the present invention may also be used as desizing agent compositions for fibers by incorporating an enzyme such as pullulanase, isoamylase or neopullulanase.

EXAMPLES

Determination of Amylase Activity and Protein Content:

The amylase activity and protein content of each enzyme was determined in accordance with the following respective methods.

The determination of amylase activity was conducted by the 3,5-dinitrosalicylic acid method (DNS method). After a reaction was conducted at 50° C. for 15 minutes in a reaction mixture with soluble starch contained in a 50 mM glycine buffer (pH: 10), reducing sugar formed was determined by the DNS method. With respect to the enzymatic activity, the amount of the enzyme, which forms reducing sugar corresponding to 1 μmol of glucose for 1 minute, was defined as 1 unit.

The protein content was determined by means of a Protein Assay Kit produced by Bio-Rad Laboratories making use of bovine serum albumin as a standard.

Referential Example 1

Screening of Liquefying Alkaline Amylase:

Soil (about 0.5 g) was suspended in sterilized water and subjected to a heat treatment at 80° C. for 15 minutes. A supernatant of the heat-treated suspension was suitably diluted with sterilized water, and the resultant dilute solution was coated on an agar medium (Medium A) for separation. Culture was then conducted at 30° C. for 2 days to form colonies. Those on the peripheries of which transparent halo based on amylolysis had been formed were screened, and isolated as amylase-producing bacteria. Further, the thus-isolated bacteria were inoculated on Medium B and subjected to aerobic shaking culture at 30° C. for 2 days. After the culture, the resistance performance to a chelating agent (EDTA) of a supernatant centrifugally separated was determined, and its optimum pH was further measured to screen the liquefying alkaline α-amylase-producing bacteria.

*Bacillus* sp. KSM-K38 (FERM BP-6946) and *Bacillus* sp. KSM-K36 (FERM BP-6945) strains were able to be obtained by the above-described process.

| Medium A: | Trypton | 1.5% |
|---|---|---|
| | Soyton | 0.5% |
| | Sodium chloride | 0.5% |
| | Colored starch | 0.5% |
| | Agar | 1.5% |
| | Na$_2$CO$_3$ (pH 10) | 0.5% |
| Medium B: | Trypton | 1.5% |
| | Soyton | 0.5% |
| | Sodium chloride | 0.5% |
| | Soluble starch | 1.0% |
| | Na$_2$CO$_3$ (pH 10) | 0.5% |

The mycological natures of the KSM-K38 and KSM-K36 strains are shown in Table 1.

TABLE 1

| | KSM-K36 strain | KSM-K38 strain |
|---|---|---|
| (a) Results of microscopic observation | Bacili having sizes of 1.0–1.2 μm × 2.4–5.4 μm for K36 stain and 1.0–1.2 μm × 1.8–3.8 μm for K38 strain. Oval endospores (1.0–1.2 μm × 1.2–1.4 μm) are formed at near end or the center thereof. Having periplasmic flagella and motility. Gram staining is positive. Having no acid-fast. | |
| (b) Growth state on various media: Incidentally, the strains are alkaliphilic and so 0.5% sodium carbonate was added to media used in the following tests. | | |
| Nutrient agar plate culture | Good growth state. Form of colonies is circular. Smooth surface and rough periphery. Color of colonies is pale-ocher. | Good growth state. Form of colonies is circular. Smooth surface and smooth periphery. Color of colonies is yellowish-brown. |
| Nutrient agar slant culture | Grown. | Grown. |
| Nutrient broth liquid culture | Grown. | Grown. |
| Nutrient broth gelatin stab culture | Good growth state. No gelatin liquefaction is observed. | Good growth state. No gelatin liquefaction is observed. |
| Litmus milk medium | Not changed. | Not changed. |
| (c) Physiological nature: | | |
| Reduction of nitrate and denitrification | Reduction of nitrate is positive. Denitrification is negative. | Reduction of nitrate is positive. Denitrification is negative. |
| MR test | Failed to judge because the medium is alkaline. | Failed to judge because the medium is alkaline. |
| V-P test | Negative. | Negative. |
| Formation of indole | Negative. | Negative. |
| Formation of hydrogen sulfide | Negative. | Negative. |
| Hydrolysis of starch | Negative. | Negative. |
| Citrate utilization | Grown on Christensen medium but not grown on Cocer and Simmons media. | Grown on Christensen medium but not grown on Cocer and Simmons media. |
| Utilization of inorganic nitrogen source | Nitrate is utilized, but ammonium salt is not utilized. | Nitrate is utilized, but ammonium salt is not utilized. |
| Formation of pigment | Formation of pale-yellow pigment on King B medium. | Negative. |
| Urease | Negative | Negative |
| Oxidase | Negative | Negative |

TABLE 1-continued

|  | KSM-K36 strain | KSM-K38 strain |
|---|---|---|
| Catalase | Negative | Negative |
| Range of growth | Temperature range for growth is 15–40° C., and optimum temperature range for growth is 30–37° C. pH range for growth is pH 8.0–11.0, and optimum pH for growth is pH 10.0–11.0. | Temperature range for growth is 15–40° C., and optimum temperature for growth is 30° C. pH range for growth is pH 9.0–11.0, and optimum pH for growth is the same as described above. |
| Behavior against oxygen | Aerobic. | Aerobic. |
| O-F test | Not grown. | Not grown. |
| Sugar utilization | D-galactose, D-xylose, L-arabinose, lactose, glycerol, melibiose, ribose, D-glucose, D-mannose, maltose, sucrose, trehalose, D-mannit, starch, raffinose and D-fructose are utilized. | |
| Growth on salt-containing medium | Grown at a salt concentration of 12%, but not grown at a concentration of 15%. | |

Reference Example 2

Culture of KSM-K38 and KSM-K36 Strains:

The KSM-K38 or KSM-K36 strain was inoculated on the liquid medium B used in Referential Example 1 to conduct shaking culture at 30° C. for 2 days. The amylase activity (at pH 8.5) of a supernatant centrifugally separated was determined. As a result, these strains had activities of 557 U and 1177 Upper liter of the medium, respectively.

Referential Example 3

Purification of Liquefying Alkaline Amylase:

Ammonium sulfate was added to the resultant culture supernatant of the KSM-38 strain obtained in Referential Example 2 to 80% saturation. After stirring the resultant mixture, precipitate formed was collected and dissolved in 10 mM Tris-hydrochloride buffer (pH: 7.5) containing 2 mM $CaCl_2$ and dialyzed overnight against the same buffer. The dialyzate thus obtained was passed through a DEAE-Toyopearl 650M column equilibrated with the same buffer and caused to be adsorbed on the column, and the intended enzyme was eluted with the same buffer by 0–1 M gradient of sodium chloride concentration. After the active fraction was dialyzed against the same buffer, an active fraction obtained by gel filtration column chromatography was dialyzed against the above-described buffer, thereby obtaining a purified enzyme which gave a single band on both polyacrylamide gel electrophoresis (gel concentration: 10%) and sodium dodecyl sulfate (SDS) electrophoresis. Incidentally, a purified enzyme was also able to be obtained from the culture supernatant of the KSM-K36 strain in accordance with the same process as described above.

Reference Example 4

Properties of Enzyme:

(1) Action:

Both enzymes decompose the α-1,4-glycoside bonds of starch, amylose, amylopectin and partially decomposed products thereof and produce glucose (G1), maltose (G2), maltotriose (G3), maltotetraose (G4), maltopentaose (G5), maltohexaose (G6) and maltoheptaose (G7) from amylose. However, the enzymes do not act on pullulan.

(2) pH stability (Britton-Robinson's buffer):

Both enzymes exhibit a residual activity of at least 70% in a pH range of 6.5 to 11 under treatment conditions of 40° C. and 30 minutes.

(3) Action temperature range and optimum action temperature:

Both enzymes act in a wide temperature range of 20 to 80° C. and have an optimum action temperature of 50 to 60° C.

(4) Temperature stability:

Enzyme was incubated in a 50 mM glycine-sodium hydroxide buffer (pH: 10) at various temperature for 30 minutes and then residual anzymatic activity was measured. As a result, both enzymes showed a residual activity of at least 80% at 40° C. and a residual activity of about 60% even at 45° C.

(5) Molecular weight:

Both enzymes have a molecular weight of 55,000±5,000 as measured by sodium dodecyl sulfate polyacrylamide gel electrophoresis.

(6) Isoelectric point:

Both enzymes have an isoelectric point of about 4.2 as measured by isoelectric focusing.

(7) Influence of surfactant:

Even when both enzymes are treated at pH 10 and 30° C. for 30 minutes in a 0.1% solution of each of various surfactants such as sodium linear alkylbenzenesulfonates, sodium alkylsulfates, sodium polyoxyethylene alkylsulfates, sodium α-olefinsulfonates, the sodium salts of α-sulfonated fatty acid esters, sodium alkylsulfonates, SDS, soap and Softanol, they scarcely undergo inhibition of their activities (residual activity: at least 90%).

(8) Influence of metal salt:

Both enzymes were treated at pH 10 and 30° C. for 30 minutes with each of various metal salts, thereby determining the influence thereof.

The K38 strain is inhibited by 1 mM $Mn^{2+}$ (inhibitory rate: about 75%) and somewhat inhibited by both 1 mM $Sr^{2+}$ and $Cd^{2+}$ (inhibitory rate: 30 to 40%).

Example 1

Cloning of Liquefying α-Amylase Gene

A chromosome DNA extracted from cells of the KSM-K38 strain in accordance with the method by Saito & Miura (Biochim. Biophys. Acta, 72, 619, 1961) was used as a template to amplify a gene fragment (about 1.5 kb) encoding a liquefying alkaline α-amylase (hereinafter referred to as "K38AMY") having an amino acid sequence set forth in SEQ ID NO:1 by PCR making use of primers K38US (SEQ ID NO: 19) and K38DH (SEQ ID NO: 20). The thus-amplified fragment was cleaved with a restriction enzyme Sal I, and then inserted into a Sal I-Sma I site of an expression vector pHSP64 (Japanese Patent Application Laid-Open No. 217781/1994), thereby preparing a recombinant plasmid pHSP-K38 with a structural gene of K38AMY bonded to a trailing end of a potent promoter derived from the alkaline cellulase gene of a Bacillus sp. KSM-64 (FERM P-10482) strain contained in pHSP64 (FIG. 1).

Similarly, a gene fragment (about 1.5 kb) encoding a liquefying alkaline α-amylase (hereinafter referred to as "LAMY") having an amino acid sequence set forth in SEQ ID NO:2, which had been obtained by using a chromosome DNA extracted from cells of a *Bacillus* sp. KSM-AP1378 (FERM BP-3048) strain (Japanese Patent Application Laid-Open No. 336392/1998) as a template, and amplified by PCR making use of primers LAUS (SEQ ID NO: 21) and LADH (SEQ ID NO: 22) was inserted into a Sal I-Sma I site of an expression vector pHSP64 in the same manner as described above, thereby preparing a recombinant plasmid pHSP-LAMY (FIG. 1).

Example 2

Preparation of Mutant K38AMY Gene-1

Figure 2:
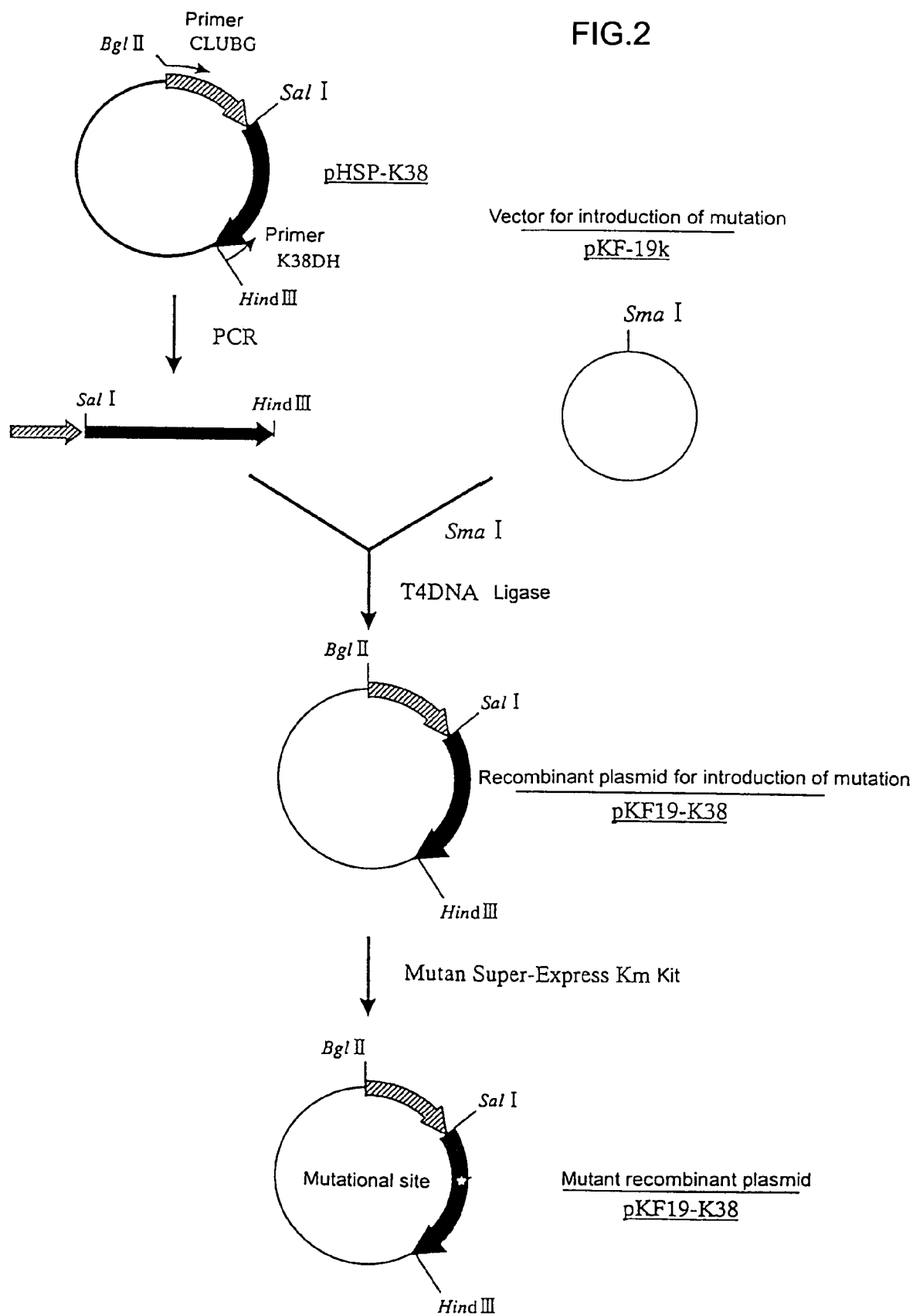
FIG. 2 illustrates a method for introducing a mutation into an α-amylase gene derived from the KSM-38 strain.

A Site-Directed Mutagenesis System Mutan-Super Express Km Kit produced by Takara Shuzo Co., Ltd. was used for a site-specific mutation. The recombinant plasmid pHSP-K38 obtained in Example 1 was first used as a template to conduct PCR making use of primers CLUBG (SEQ ID NO: 23) and K38DH (SEQ ID NO: 20), thereby amplifying a fragment of about 2.1 kb from the leading end of a potent promoter derived from the KSM-64 strain to the trailing end of the liquefying alkaline α-amylase gene. This fragment was inserted into a Sma I site of a plasmid vector pKF19k attached to the above kit to prepare a recombinant plasmid pKF19-K38 for introduction of mutation (FIG. 2).

After various kinds of oligonucleotide primers for introduction of site-specific mutation respectively set forth in SEQ ID NO:6 to NO:15 were 5'-phosphorylated with a T4 DNA kinase, each of the resultant products and pKF19-K38 were used to conduct a mutation-introducing reaction in accordance with a method described in the kit, and an *Escherichia coli* MV1184 strain (Competent Cell MV1184, product of Takara Shuzo Co., Ltd.) was transformed with the resultant reaction product. Recombinant plasmids were extracted from the resultant transformants to conduct base sequence analysis, thereby confirming the mutation.

The mutation-introduced gene was made a template plasmid upon introduction of a different mutation by inserting an expression promoter region and a mutant K38AMY gene portion into the Sma I site of pKF19k again, thereby introducing another mutation in accordance with the same process as described above.

Each of the thus-obtained mutant recombinant plasmids was used as a template to conduct PCR making use of primers CLUBG (SEQ ID NO: 23) and K38DH (SEQ ID NO: 20), thereby amplifying each of mutant K38AMY gene fragments. This fragment was cleaved with a Sal I and then inserted into a Sal I-Sma I site of an expression vector pHSP64 (Japanese Patent Application Laid-Open No. 217781/1994) to prepare a plasmid for production of mutant K38AMY (FIG. 1).

Example 3

Preparation of Mutant K38AMY Gene-2 (Chimera with LAMY Gene)

Figure 3:
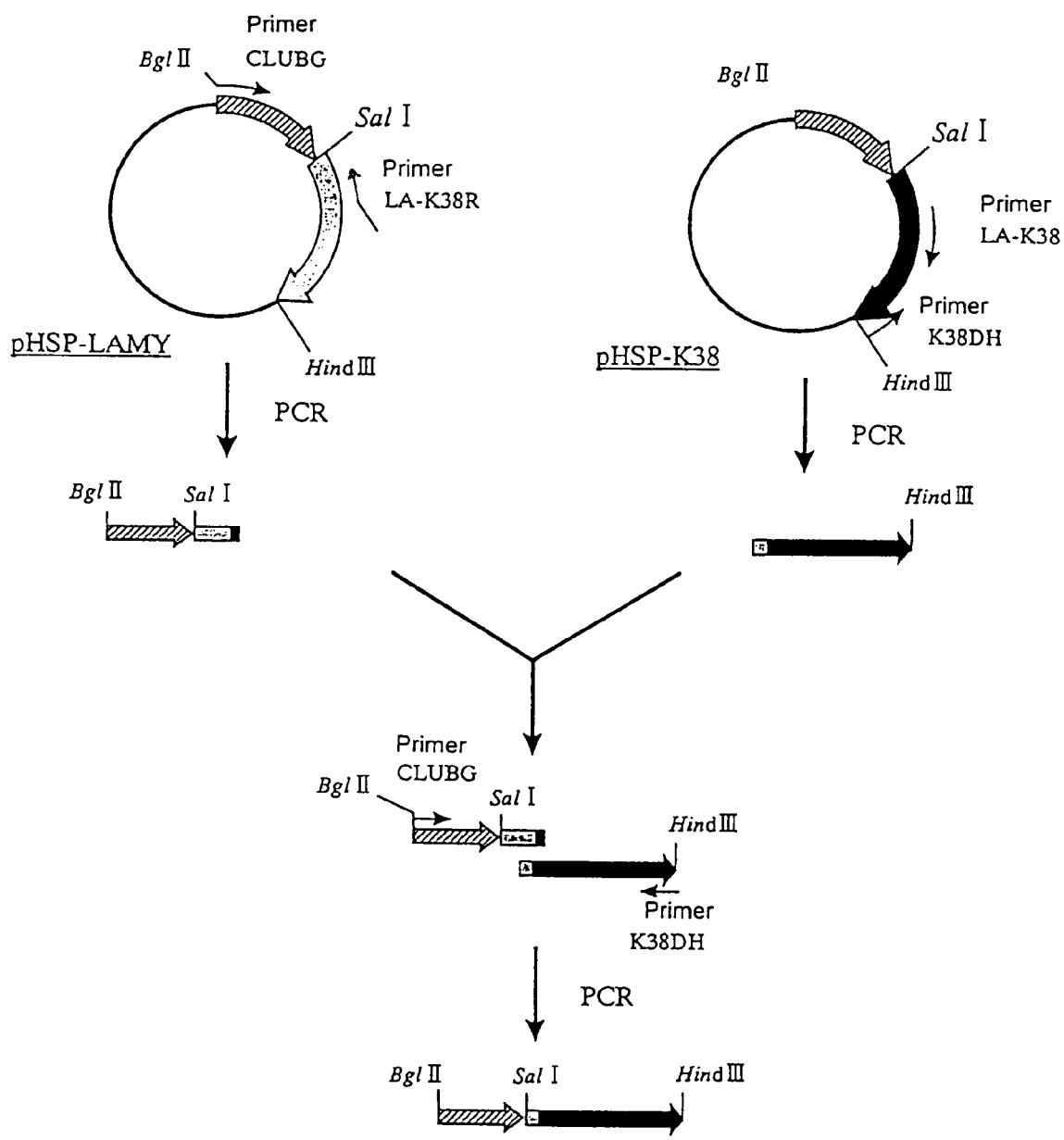
FIG. 3 illustrates a method for replacing an N-terminal sequence of the α-amylase gene derived from the KSM-38 strain by an N-terminal region of an α-amylase gene derived from the KSM-AP1378 strain.

Recombinant PCR was used for a mutation in which the N-terminal region of the K38AMY gene is replaced by its corresponding region of an LAMY gene (FIG. 3). The recombinant plasmid pHSP-K38 obtained in Example 1 was first used as a template to conduct PCR making use of primers K38DH (SEQ ID NO: 20) and LA-K38 (SEQ ID NO: 17), thereby amplifying a fragment encoding a sequence from the 20th Gln to C-terminal of the amino acid sequence of K38AMY set forth in SEQ ID NO: 1. On the other hand, the recombinant plasmid pHSP-LAMY was used as a template to conduct PCR making use of primers CLUBG (SEQ ID NO: 23) and LA-K38R (SEQ ID NO: 18), thereby amplifying a gene fragment encoding a sequence from the leading end of the potent promoter to the 21st Gly of the amino acid sequence of LAMY set forth in SEQ ID NO: 2. Second PCR making use of both DMA fragments, and primers CLUBG (SEQ ID NO: 23) and K38DH (SEQ ID NO: 20) was conducted, thereby amplifying a gene fragment (about 2.1 kb) encoding a substituted mutant enzyme (hereinafter abbreviated as "LA-K38AMY") in which both fragments having respective complementary sequences derived from the primers LA-K38 (SEQ ID NO: 17) and LA-K38R (SEQ ID NO: 18) were bonded to the terminal, and a region encoding a sequence from the 1st His to the 21st Gly of LAMY and successively a region encoding a sequence from the 20th Gln to the C-terminal of K38AMY were bonded to the trailing end of the potent promoter. This gene fragment was cleaved with Sal I and inserted into a Sal I-Sma I site of an expression vector pHSP64 (Japanese Patent Application Laid-Open No. 217781/1994), thereby preparing a plasmid for production of mutant K38AMY (FIG. 1).

Example 4

Production of Mutant Liquefying Alkaline α-Amylase

Each of the various plasmids for production of mutant K38AMY obtained in Examples 2 and 3 was introduced into a *Bacillus subtilis* ISW 1214 strain (leuA metB5 hsdM1) in accordance with the protoplast method (Mol. Gen. Genet., 168, 111, 1979) to culture the resultant recombinant *Bacillus subtilis* at 30° C. for 3 days in a liquid medium (containing 8% of corn steep liquor; 1% of meat extract; 0.02% of potassium primary phosphate; 5% of maltose; 5 mM of calcium chloride; and 15 μg/mL of tetracycline). The resultant culture supernatant was dialyzed against a Tris-HCl buffer (pH: 7.0), and the dialyzate was caused to be adsorbed on a DEAE-Toyopearl 650M column equilibrated with the same buffer, and eluted by gradient of NaCl concentration. This eluate was dialyzed against a 10 mM glycine buffer (pH: 10.0), thereby obtaining a purified enzyme of each mutant K38AMY.

Example 5

Assay of Heat Resistance-1

Purified preparations of an enzyme (abbreviated as "Y11F") with the 11th Tyr in SEQ ID NO:1 replaced by Phe, an enzyme (abbreviated as "N49S") with the 49th Asn replaced by Ser, an enzyme (abbreviated as "E84Q") with the 84th Glu replaced by Gln, an enzyme (abbreviated as "S144P") with the 144th Ser replaced by Pro, an enzyme (abbreviated as "Q167E") with the 167th Gln replaced by Glu, an enzyme (abbreviated as "Y169K") with the 169th Tyr replaced by Lys, an enzyme (abbreviated as "A178Q") with the 178th Ala replaced by Gln, an enzyme (abbreviated as "E188D") with the 188th Glu replaced by Asp, an enzyme (abbreviated as "N190F") with the 190th Asn replaced by Phe, and an enzyme (abbreviated as "Q209V") with the 209th Gln replaced by Val were obtained in accordance with the processes described in Examples 1, 2 and 4, and their heat resistance was assayed by the following method. As a control, wild type K38AMY was used.

Each enzyme was added to a 50 mM glycine buffer (pH: 10.0) preincubated at 50° C. so as to give a concentration of about 1.2 U/mL, and after 30 minutes, the buffer was sampled to determine the residual amylase activity of the enzyme in accordance with the method described above in EXAMPLES. The activity of the enzyme at the start is regarded as 100% to determine a relative activity, thereby regarding it as the residual amylase activity. The results are shown in Table 2. In the wild type K38AMY, the residual activity was decreased to 15%, while all the mutant enzymes exhibited a high residual activity compared with the wild type.

TABLE 2

| Enzyme | Residual activity (%) after 30 minutes |
|---|---|
| Wild type | 15 |
| Y11F | 40 |
| N49S | 30 |
| E84Q | 25 |
| S144P | 30 |
| Q167E | 46 |
| Y169K | 63 |
| A178Q | 20 |
| E188D | 30 |
| N190F | 70 |
| Q209V | 40 |

Example 6

Assay of Heat Resistance-2

Mutant enzymes with Q167E, Y169K, N190F and Q209V among the mutations described in Example 5 combined in the following manner were prepared in accordance with the processes described in Examples 1, 2 and 4.

Q167E/Y169K (abbreviated as "QEYK", prepared by using primer of SEQ ID NO: 16)

N190F/Q209V (abbreviated as "NFQV")

Q167E/Y169K/N190F/Q209V (abbreviated as "QEYK/NFQV")

With respect to these enzymes, the heat resistance was assayed by a method similar to Example 5. However, the temperature in the heat treatment was changed to 55° C., and Q167E, Y169K, N190F and Q209V were used as controls. As a result, as shown in Table 3, all the mutants were observed being improved in heat resistance by the combination, and QEYK/NFQV obtained by combining 4 mutations exhibited a residual activity of 85% after 30 minutes even at 55° C.

TABLE 3

| Enzyme | Residual activity (%) after 30 minutes |
|---|---|
| Q167E | 7 |
| Y169K | 14 |
| QEYK | 45 |
| N190F | 20 |
| Q209V | 1 |
| NFQV | 40 |
| QEYK/NFQV | 85 |

Example 7

Assay of Heat Resistance-3

The following mutant enzymes with the mutation NFQV described in Example 6 combined with S144P described in Example 5, and further combined with a mutation of replacement of 16th Gln by Pro (abbreviated as "E16P") were prepared in accordance with the processes described in Examples 1, 2 and 4.

S144P/NFQV (abbreviated as "SP/NFQV")

E16P/S144P/NFQV (abbreviated as "EPSP/NFQV")

With respect to these enzymes, the heat resistance was assayed by a method (50° C.) similar to Example 5. As a result, as shown in Table 4, improvement in heat resistance was observed by combining E16P with SP/NFQV.

TABLE 4

| Enzyme | Residual activity (%) after 30 minutes |
|---|---|
| SP/NFQV | 40 |
| EPSP/NFQV | 50 |

Example 8

Assay of Heat Resistance-4

The following mutant enzymes with QEYK/NFQV among the mutations described in Example 6 suitably combined with a mutation (abbreviated as "M107L") with the 107th Met in SEQ ID NO:1 replaced by Leu, a mutation (abbreviated as "H205R") with the 205th His replaced by Arg, and N49S among the mutations described in Example 5 were prepared in accordance with the processes described in Examples 1, 2 and 4.

M107L/QEYK/NFQV (abbreviated as "ML/QEYK/NFQV")

N49S/M107L/QEYK/NFQV (abbreviated as "NSML/QEYK/NFQV")

N49S/M107L/H205R/QEYK/NFQV (abbreviated as "NSMLHR/QEYK/NFQV")

With respect to these enzymes, the heat resistance was assayed by a method similar to Example 5. However, the temperature in the heat treatment was changed to 60° C.

As a result, heat resistance was additionally improved by combining ML/QEYK/NFQV with N49S, further H205R, and NSMLHR/QEYK/NFQV exhibited a residual activity of 75% after 30 minutes even at 60° C. (Table 5)

TABLE 5

| Enzyme | Residual activity (%) after 30 minutes |
|---|---|
| ML/QEYK/NFQV | 30 |
| NSML/QEYK/NFQV | 50 |
| NSMLHR/QEYK/NFQV | 75 |

Example 9

Assay of Heat Resistance-5

A mutant enzyme LA-K38AMY with a sequence from the 1st Asp to the 19th Gly of K38AMY replaced by a sequence from the 1st His to the 21st Gly of LAMY was obtained in accordance with the processes described in Examples 1, 3 and 4. The heat resistance of this enzyme was assayed by the method described in Example 5. As a result, as shown in Table 6, improvement in heat resistance by the replacement was observed.

TABLE 6

| Enzyme | Residual activity (%) after 30 minutes |
|---|---|
| Wild type | 15 |
| LA-K38AMY | 33 |

Example 10

Assay of Heat Resistance-6

Into the gene of the mutant enzyme QEYK/NFQV described in Example 6, was introduced a mutation with a sequence from the 1st Asp to the 19th Gly replaced by a sequence from the 1st His to the 21st Gly of LAMY in accordance with the same processes as in Examples 1 and 3. With respect to a mutant enzyme LA-K38AMY/QEYK/NFQV obtained by using this enzyme in accordance with the process described in Example 4, the heat resistance was assayed by the same method (heat treatment temperature: 60° C.) as in Example 8.

As a result, heat resistance was additionally improved by the combination, and LA-K38AMY/QEYK/NFQV exhibited a residual activity of 63% after 30 minutes even at 60° C. (Table 7)

TABLE 7

| Enzyme | Residual activity (%) after 30 minutes |
|---|---|
| LA-K38AMY | 1 |
| QEYK/NFQV | 40 |
| LA-K38AMY/QEYK/NFQV | 63 |

Example 11

Detergent Composition for Automatic Dish Washer

A detergent composition for automatic dish washer was produced in accordance with a formulation shown in Table 8, and various mutant enzymes were separately incorporated into this detergent composition to conduct a washing test. As a result, the mutant enzymes exhibited an excellent detergent effect compared with the wild type enzyme when the enzymes having the same activity value as each other are added.

TABLE 8

| Composition of detergent | (%) |
|---|---|
| Pluronic L-61 | 2.2 |
| Sodium carbonate | 24.7 |
| Sodium hydrogencarbonate | 24.7 |
| Sodium percarbonate | 10.0 |
| Sodium silicate No. 1 | 12.0 |
| Trisodium citrate | 20.0 |
| Polypropylene glycol | 2.2 |
| Silicone KST-04 (product of Toshiba silicone Co., Ltd.) | 0.2 |
| Socarane CP-A45 (product of BASF AG) | 4.0 |

The mutant α-amylases according to the present invention have excellent properties of high resistance to chelating agents, high specific activity in an alkaline region, excellent stability to heat, and are hence useful for detergents for automatic dish washer, laundry detergents, compositions for liquefaction and saccharification of starch, and desizing agents for fibers.

What is claimed is:

1. A mutant α-amylase obtained by introducing a mutation into SEQ ID NO:1,
   wherein said mutation consists of:
   the substitution of an amino acid residue selected from the group consisting of: the $11^{th}$ Tyr, $16^{th}$ Glu, $49^{th}$ Asn, $84^{th}$ Glu, $144^{th}$ Ser, $167^{th}$ Gln, $169^{th}$ Tyr, $178^{th}$ Ala, $188^{th}$ Glu, $190^{th}$ Asn, $205^{th}$ His and $209^{th}$ Gln, with another amino acid, and optionally an additional substitution of an amino acid residue at 107th Met with Leu.

2. The mutant α-amylase according to claim 1, wherein the $11^{th}$ Tyr of SEQ ID NO:1 is substituted with Phe, the $16^{th}$ Glu of SEQ ID NO:1 is substituted with Pro, the $49^{th}$ Asn of SEQ ID NO:1 is substituted with Ser, the 84th Glu of SEQ ID NO:1 is substituted with Gln, the 144th Ser of SEQ ID NO:1 is substituted with Pro, the 167 Gln of SEQ ID NO:1 is substituted with Glu, the 169$^{th}$ Tyr of SEQ ID NO:1 is substituted with Lys, the 178th Ala of SEQ ID NO:1 is substituted with Gln, the 188th Glu of SEQ ID NO:1 is substituted Asp, the 190$^{th}$ Asn of SEQ ID NO:1 is substituted with Phe, the 205$^{th}$ His of SEQ ID NO:1 is substituted with Arg, and the 209$^{th}$ Gln of SEQ ID NO:1 is substituted with Val.

3. A mutant α-amylase obtained by introducing a mutation into SEQ ID NO:1, and wherein said mutation consists of:

substituting the N-amino terminal sequence from 1$^{st}$ Asp through 19$^{th}$ Gly of SEQ ID NO:1 with the amino acid sequence from 1$^{st}$ His to 21$^{st}$ Gly of SEQ ID NO:2.

4. A mutant α-amylase obtained by introducing a mutation into SEQ ID NO:1, wherein said mutation consists of:

the substitution of an amino acid residue selected from the group consisting of: 167$^{th}$ Gln and 169$^{th}$ Tyr with another amino acid.

5. A mutant α-amylase obtained by introducing a mutation into SEQ ID NO:1, wherein said mutation consists of:

the substitution of an amino acid residue selected from the group consisting of: 190$^{th}$ Asn and 209$^{th}$ Gln with another amino acid.

6. A mutant α-amylase obtained by introducing a mutation into SEQ ID NO:1, wherein said mutation consists of:

the substitution of an amino acid residue selected from the group consisting of: 167$^{th}$ Gln, 169$^{th}$ Tyr, 190$^{th}$ Asn, and 209$^{th}$ Gln with another amino acid.

7. A mutant α-amylase obtained by introducing the following mutations into SEQ ID NO:1:

the substitution of 167$^{th}$ Gln, 169$^{th}$ Tyr, 190$^{th}$ Asn, and 209$^{th}$ Gln with another amino acid, and 107$^{th}$ Met with Leu.

8. A mutant α-amylase obtained by introducing the following mutations into SEQ ID NO:1:

the substitution of 49$^{th}$ Asn, 167$^{th}$ Gln, 169$^{th}$ Tyr, 190$^{th}$ Asn, and 209$^{th}$ Gln with another amino acid, and 107$^{th}$ Met with Leu.

9. A mutant α-amylase obtained by introducing the following mutations into SEQ ID NO:1:

the substitution of 49$^{th}$ Asn, 205$^{th}$ His, 167$^{th}$ Gln, 169$^{th}$ Tyr, 190$^{th}$ Asn, and 209$^{th}$ Gln with another amino acid, and 107$^{th}$ Met with Leu.

10. The mutant α-amylase according to claim 4, wherein the 167$^{th}$ Gln is substituted with Glu, and wherein said 169$^{th}$ Tyr is substituted with Lys.

11. The mutant α-amylase according to claim 5, wherein the 190$^{th}$ Asn is substituted with Phe, and wherein said 209$^{th}$ Gln is substituted with Val.

12. The mutant α-amylase according to claim 6, wherein the 167$^{th}$ Gln is substituted with Glu, the 169$^{th}$ Tyr is substituted with Lys, the 190$^{th}$ Asn is substituted with Phe, and wherein said 209$^{th}$ Gln is substituted with Val.

13. The mutant α-amylase according to claim 7, wherein the 107$^{th}$ Met is substituted with Leu, the 167$^{th}$ Gln is substituted with Glu, the 169$^{th}$ Tyr is substituted with Lys, the 190$^{th}$ Asn is substituted with Phe, and wherein said 209$^{th}$ Gln is substituted with Val.

14. The mutant α-amylase according to claim 8, wherein the 49$^{th}$ Asn is substituted with Ser, the 107$^{th}$ Met is substituted with Leu, the 167$^{th}$ Gln is substituted with Glu, the 169$^{th}$ Tyr is substituted with Lys, the 190$^{th}$ Asn is substituted with Phe, and wherein said 209$^{th}$ Gln is substituted with Val.

15. The mutant α-amylase according to claim 9, wherein the 49$^{th}$ Asn is substituted with Ser, the 107$^{th}$ Met is substituted with Leu, the 167$^{th}$ Gln is substituted with Glu, the 169$^{th}$ Tyr is substituted with Lys, the 190$^{th}$ Asn is substituted with Phe, the 205$^{th}$ His is substituted with Arg, and wherein said 209$^{th}$ Gln is substituted with Val.

16. A mutant α-amylase obtained by introducing the following mutations into SEQ ID NO:1 the substitution of 167$^{th}$ Gln, 169$^{th}$ Tyr, 190$^{th}$ Asn, and 209$^{th}$ Gln with Glu, Lys, Phe, and Val, respectively, and the substitution of the N-amino terminal sequence from 1$^{st}$ Asp through 19$^{th}$ Gly of SEQ ID NO:1 with the amino acid sequence from 1$^{st}$ His to 21$^{st}$ Gly of SEQ ID NO:2.

17. A mutant α-amylase obtained by introducing a mutation into SEQ ID NO:1, wherein said mutation consists of:

the substitution of an amino acid residue selected from the group consisting of: 144$^{th}$ Ser, 190$^{th}$ Asn, and 209$^{th}$ Gln with another amino acid.

18. The mutant α-amylase according to claim 17, wherein the 144$^{th}$ Ser is substituted with Pro, the 190$^{th}$ Asn is substituted with Phe, and wherein said 209$^{th}$ Gln is substituted with Val.

19. A mutant α-amylase obtained by introducing a mutation into SEQ ID NO:1, wherein said mutation consists of:

the substitution of an amino acid residue selected from the group consisting of: 16$^{th}$ Glu, 144$^{th}$ Ser, 190$^{th}$ Asn, and 209$^{th}$ Gln with another amino acid.

20. The mutant α-amylase according to claim 19, wherein the 16$^{th}$ Glu is substituted with Pro, the 144$^{th}$ Ser is substituted with Pro, the 190$^{th}$ Asn is substituted with Phe, and wherein said 209$^{th}$ Gln is substituted with Val.

* * * * *

SEQUENCE LISTING

```
<160> NUMBER OF SEQ ID NOS: 23

<210> SEQ ID NO 1
<211> LENGTH: 480
<212> TYPE: PRT
<213> ORGANISM: Bacillus sp. KSM-K38

<400> SEQUENCE: 1

Asp Gly Leu Asn Gly Thr Met Met Gln Tyr Tyr Glu Trp His Leu Glu
                 5                  10                  15

Asn Asp Gly Gln His Trp Asn Arg Leu His Asp Asp Ala Ala Ala Leu
             20                  25                  30

Ser Asp Ala Gly Ile Thr Ala Ile Trp Ile Pro Pro Ala Tyr Lys Gly
         35                  40                  45

Asn Ser Gln Ala Asp Val Gly Tyr Gly Ala Tyr Asp Leu Tyr Asp Leu
     50                  55                  60

Gly Glu Phe Asn Gln Lys Gly Thr Val Arg Thr Lys Tyr Gly Thr Lys
 65                  70                  75                  80

Ala Gln Leu Glu Arg Ala Ile Gly Ser Leu Lys Ser Asn Asp Ile Asn
                 85                  90                  95

Val Tyr Gly Asp Val Val Met Asn His Lys Met Gly Ala Asp Phe Thr
```

```
              100                 105                 110
Glu Ala Val Gln Ala Val Gln Val Asn Pro Thr Asn Arg Trp Gln Asp
            115                 120                 125
Ile Ser Gly Ala Tyr Thr Ile Asp Ala Trp Thr Gly Phe Asp Phe Ser
130                 135                 140
Gly Arg Asn Asn Ala Tyr Ser Asp Phe Lys Trp Arg Trp Phe His Phe
145                 150                 155                 160
Asn Gly Val Asp Trp Asp Gln Arg Tyr Gln Glu Asn His Ile Phe Arg
                165                 170                 175
Phe Ala Asn Thr Asn Trp Asn Trp Arg Val Asp Glu Glu Asn Gly Asn
            180                 185                 190
Tyr Asp Tyr Leu Leu Gly Ser Asn Ile Asp Phe Ser His Pro Glu Val
            195                 200                 205
Gln Asp Glu Leu Lys Asp Trp Gly Ser Trp Phe Thr Asp Glu Leu Asp
210                 215                 220
Leu Asp Gly Tyr Arg Leu Asp Ala Ile Lys His Ile Pro Phe Trp Tyr
225                 230                 235                 240
Thr Ser Asp Trp Val Arg His Gln Arg Asn Glu Ala Asp Gln Asp Leu
                245                 250                 255
Phe Val Val Gly Glu Tyr Trp Lys Asp Asp Val Gly Ala Leu Glu Phe
            260                 265                 270
Tyr Leu Asp Glu Met Asn Trp Glu Met Ser Leu Phe Asp Val Pro Leu
            275                 280                 285
Asn Tyr Asn Phe Tyr Arg Ala Ser Gln Gln Gly Gly Ser Tyr Asp Met
            290                 295                 300
Arg Asn Ile Leu Arg Gly Ser Leu Val Glu Ala His Pro Met His Ala
305                 310                 315                 320
Val Thr Phe Val Asp Asn His Asp Thr Gln Pro Gly Glu Ser Leu Glu
                325                 330                 335
Ser Trp Val Ala Asp Trp Phe Lys Pro Leu Ala Tyr Ala Thr Ile Leu
            340                 345                 350
Thr Arg Glu Gly Gly Tyr Pro Asn Val Phe Tyr Gly Asp Tyr Tyr Gly
            355                 360                 365
Ile Pro Asn Asp Asn Ile Ser Ala Lys Lys Asp Met Ile Asp Glu Leu
370                 375                 380
Leu Asp Ala Arg Gln Asn Tyr Ala Tyr Gly Thr Gln His Asp Tyr Phe
385                 390                 395                 400
Asp His Trp Asp Val Val Gly Trp Thr Arg Glu Gly Ser Ser Ser Arg
                405                 410                 415
Pro Asn Ser Gly Leu Ala Thr Ile Met Ser Asn Gly Pro Gly Gly Ser
            420                 425                 430
Lys Trp Met Tyr Val Gly Arg Gln Asn Ala Gly Gln Thr Trp Thr Asp
            435                 440                 445
Leu Thr Gly Asn Asn Gly Ala Ser Val Thr Ile Asn Gly Asp Gly Trp
            450                 455                 460
Gly Glu Phe Phe Thr Asn Gly Gly Ser Val Ser Val Tyr Val Asn Gln
465                 470                 475                 480

<210> SEQ ID NO 2
<211> LENGTH: 485
<212> TYPE: PRT
<213> ORGANISM: Bacillus sp. KSM-AP1378

<400> SEQUENCE: 2
```

-continued

```
His His Asn Gly Thr Asn Gly Thr Met Met Gln Tyr Phe Glu Trp His
              5                  10                  15
Leu Pro Asn Asp Gly Asn His Trp Asn Arg Leu Arg Asp Asp Ala Ala
             20                  25                  30
Asn Leu Lys Ser Lys Gly Ile Thr Ala Val Trp Ile Pro Pro Ala Trp
         35                  40                  45
Lys Gly Thr Ser Gln Asn Asp Val Gly Tyr Gly Ala Tyr Asp Leu Tyr
     50                  55                  60
Asp Leu Gly Glu Phe Asn Gln Lys Gly Thr Val Arg Thr Lys Tyr Gly
 65                  70                  75                  80
Thr Arg Ser Gln Leu Gln Gly Ala Val Thr Ser Leu Lys Asn Asn Gly
                 85                  90                  95
Ile Gln Val Tyr Gly Asp Val Val Met Asn His Lys Gly Gly Ala Asp
             100                 105                 110
Gly Thr Glu Met Val Asn Ala Val Glu Val Asn Arg Ser Asn Arg Asn
         115                 120                 125
Gln Glu Ile Ser Gly Glu Tyr Thr Ile Glu Ala Trp Thr Lys Phe Asp
     130                 135                 140
Phe Pro Gly Arg Gly Asn Thr His Ser Asn Phe Lys Trp Arg Trp Tyr
145                 150                 155                 160
His Phe Asp Gly Thr Asp Trp Asp Gln Ser Arg Gln Leu Gln Asn Lys
                 165                 170                 175
Ile Tyr Lys Phe Arg Gly Thr Gly Lys Ala Trp Asp Trp Glu Val Asp
             180                 185                 190
Ile Glu Asn Gly Asn Tyr Asp Tyr Leu Met Tyr Ala Asp Ile Asp Met
         195                 200                 205
Asp His Pro Glu Val Ile Asn Glu Leu Arg Asn Trp Gly Val Trp Tyr
     210                 215                 220
Thr Asn Thr Leu Asn Leu Asp Gly Phe Arg Ile Asp Ala Val Lys His
225                 230                 235                 240
Ile Lys Tyr Ser Tyr Thr Arg Asp Trp Leu Thr His Val Arg Asn Thr
                 245                 250                 255
Thr Gly Lys Pro Met Phe Ala Val Ala Glu Phe Trp Lys Asn Asp Leu
             260                 265                 270
Ala Ala Ile Glu Asn Tyr Leu Asn Lys Thr Ser Trp Asn His Ser Val
         275                 280                 285
Phe Asp Val Pro Leu His Tyr Asn Leu Tyr Asn Ala Ser Asn Ser Gly
     290                 295                 300
Gly Tyr Phe Asp Met Arg Asn Ile Leu Asn Gly Ser Val Val Gln Lys
305                 310                 315                 320
His Pro Ile His Ala Val Thr Phe Val Asp Asn His Asp Ser Gln Pro
                 325                 330                 335
Gly Glu Ala Leu Glu Ser Phe Val Gln Ser Trp Phe Lys Pro Leu Ala
             340                 345                 350
Tyr Ala Leu Ile Leu Thr Arg Glu Gln Gly Tyr Pro Ser Val Phe Tyr
         355                 360                 365
Gly Asp Tyr Tyr Gly Ile Pro Thr His Gly Val Pro Ser Met Lys Ser
     370                 375                 380
Lys Ile Asp Pro Leu Leu Gln Ala Arg Gln Thr Tyr Ala Tyr Gly Thr
385                 390                 395                 400
Gln His Asp Tyr Phe Asp His His Asp Ile Ile Gly Trp Thr Arg Glu
                 405                 410                 415
Gly Asp Ser Ser His Pro Asn Ser Gly Leu Ala Thr Ile Met Ser Asp
```

-continued

```
                    420             425             430
Gly Pro Gly Gly Asn Lys Trp Met Tyr Val Gly Lys His Lys Ala Gly
            435             440             445

Gln Val Trp Arg Asp Ile Thr Gly Asn Arg Ser Gly Thr Val Thr Ile
        450             455             460

Asn Ala Asp Gly Trp Gly Asn Phe Thr Val Asn Gly Gly Ala Val Ser
465             470             475             480

Val Trp Val Lys Gln
            485

<210> SEQ ID NO 3
<211> LENGTH: 1753
<212> TYPE: DNA
<213> ORGANISM: Bacillus sp. KSM-K38
<220> FEATURE:
<221> NAME/KEY: sig_peptide
<222> LOCATION: (162)..(224)
<221> NAME/KEY: mat_peptide
<222> LOCATION: (225)..()
<221> NAME/KEY: CDS
<222> LOCATION: (162)..(1664)

<400> SEQUENCE: 3
gtatgcgaaa cgatgcgcaa aactgcgcaa ctactagcac tcttcaggga ctaaaccacc    60 tttttttccaa aaatgacatc atataaacaa atttgtctac caatcactat ttaaagctgt   120
ttatgatata tgtaagcgtt atcattaaaa ggaggtattt g atg aga aga tgg gta   176
                                              Met Arg Arg Trp Val
                                                  -20 gta gca atg ttg gca gtg tta ttt tta ttt cct tcg gta gta gtt gca    224
Val Ala Met Leu Ala Val Leu Phe Leu Phe Pro Ser Val Val Val Ala
    -15             -10              -5              -1 gat gga ttg aac ggt acg atg atg cag tat tat gag tgg cat ttg gaa    272
Asp Gly Leu Asn Gly Thr Met Met Gln Tyr Tyr Glu Trp His Leu Glu
  1               5              10              15 aac gac ggg cag cat tgg aat cgg ttg cac gat gat gcc gca gct ttg    320
Asn Asp Gly Gln His Trp Asn Arg Leu His Asp Asp Ala Ala Ala Leu
                20              25              30 agt gat gct ggt att aca gct att tgg att ccg cca gcc tac aaa ggt    368
Ser Asp Ala Gly Ile Thr Ala Ile Trp Ile Pro Pro Ala Tyr Lys Gly
            35              40              45 aat agt cag gcg gat gtt ggg tac ggt gca tac gat ctt tat gat tta    416
Asn Ser Gln Ala Asp Val Gly Tyr Gly Ala Tyr Asp Leu Tyr Asp Leu
    50              55              60 gga gag ttc aat caa aag ggt act gtt cga acg aaa tac gga act aag    464
Gly Glu Phe Asn Gln Lys Gly Thr Val Arg Thr Lys Tyr Gly Thr Lys
65              70              75              80 gca cag ctt gaa cga gct att ggg tcc ctt aaa tct aat gat atc aat    512
Ala Gln Leu Glu Arg Ala Ile Gly Ser Leu Lys Ser Asn Asp Ile Asn
                85              90              95 gta tac gga gat gtc gtg atg aat cat aaa atg gga gct gat ttt acg    560
Val Tyr Gly Asp Val Val Met Asn His Lys Met Gly Ala Asp Phe Thr
            100             105             110 gag gca gtg caa gct gtt caa gta aat cca acg aat cgt tgg cag gat    608
Glu Ala Val Gln Ala Val Gln Val Asn Pro Thr Asn Arg Trp Gln Asp
        115             120             125 att tca ggt gcc tac acg att gat gcg tgg acg ggt ttc gac ttt tca    656
Ile Ser Gly Ala Tyr Thr Ile Asp Ala Trp Thr Gly Phe Asp Phe Ser
    130             135             140 ggg cgt aac aac gcc tat tca gat ttt aag tgg aga tgg ttc cat ttt    704
Gly Arg Asn Asn Ala Tyr Ser Asp Phe Lys Trp Arg Trp Phe His Phe
```

```
                    145                 150                 155                 160
aat ggt gtt gac tgg gat cag cgc tat caa gaa aat cat att ttc cgc         752
Asn Gly Val Asp Trp Asp Gln Arg Tyr Gln Glu Asn His Ile Phe Arg
                165                 170                 175 ttt gca aat acg aac tgg aac tgg cga gtg gat gaa gag aac ggt aat         800
Phe Ala Asn Thr Asn Trp Asn Trp Arg Val Asp Glu Glu Asn Gly Asn
                180                 185                 190 tat gat tac ctg tta gga tcg aat atc gac ttt agt cat cca gaa gta         848
Tyr Asp Tyr Leu Leu Gly Ser Asn Ile Asp Phe Ser His Pro Glu Val
            195                 200                 205 caa gat gag ttg aag gat tgg ggt agc tgg ttt acc gat gag tta gat         896
Gln Asp Glu Leu Lys Asp Trp Gly Ser Trp Phe Thr Asp Glu Leu Asp
        210                 215                 220 ttg gat ggt tat cgt tta gat gct att aaa cat att cca ttc tgg tat         944
Leu Asp Gly Tyr Arg Leu Asp Ala Ile Lys His Ile Pro Phe Trp Tyr
225                 230                 235                 240 aca tct gat tgg gtt cgg cat cag cgc aac gaa gca gat caa gat tta         992
Thr Ser Asp Trp Val Arg His Gln Arg Asn Glu Ala Asp Gln Asp Leu
                245                 250                 255 ttt gtc gta ggg gaa tat tgg aag gat gac gta ggt gct ctc gaa ttt        1040
Phe Val Val Gly Glu Tyr Trp Lys Asp Asp Val Gly Ala Leu Glu Phe
            260                 265                 270 tat tta gat gaa atg aat tgg gag atg tct cta ttc gat gtt cca ctt        1088
Tyr Leu Asp Glu Met Asn Trp Glu Met Ser Leu Phe Asp Val Pro Leu
        275                 280                 285 aat tat aat ttt tac cgg gct tca caa caa ggt gga agc tat gat atg        1136
Asn Tyr Asn Phe Tyr Arg Ala Ser Gln Gln Gly Gly Ser Tyr Asp Met
290                 295                 300 cgt aat att tta cga gga tct tta gta gaa gcg cat ccg atg cat gca        1184
Arg Asn Ile Leu Arg Gly Ser Leu Val Glu Ala His Pro Met His Ala
305                 310                 315                 320 gtt acg ttt gtt gat aat cat gat act cag cca ggg gag tca tta gag        1232
Val Thr Phe Val Asp Asn His Asp Thr Gln Pro Gly Glu Ser Leu Glu
                325                 330                 335 tca tgg gtt gct gat tgg ttt aag cca ctt gct tat gcg aca att ttg        1280
Ser Trp Val Ala Asp Trp Phe Lys Pro Leu Ala Tyr Ala Thr Ile Leu
            340                 345                 350 acg cgt gaa ggt ggt tat cca aat gta ttt tac ggt gat tac tat ggg        1328
Thr Arg Glu Gly Gly Tyr Pro Asn Val Phe Tyr Gly Asp Tyr Tyr Gly
        355                 360                 365 att cct aac gat aac att tca gct aaa aaa gat atg att gat gag ctg        1376
Ile Pro Asn Asp Asn Ile Ser Ala Lys Lys Asp Met Ile Asp Glu Leu
370                 375                 380 ctt gat gca cgt caa aat tac gca tat ggc acg cag cat gac tat ttt        1424
Leu Asp Ala Arg Gln Asn Tyr Ala Tyr Gly Thr Gln His Asp Tyr Phe
385                 390                 395                 400 gat cat tgg gat gtt gta gga tgg act agg gaa gga tct tcc tcc aga        1472
Asp His Trp Asp Val Val Gly Trp Thr Arg Glu Gly Ser Ser Ser Arg
                405                 410                 415 cct aat tca ggc ctt gcg act att atg tcg aat gga cct ggt ggt tcc        1520
Pro Asn Ser Gly Leu Ala Thr Ile Met Ser Asn Gly Pro Gly Gly Ser
            420                 425                 430 aag tgg atg tat gta gga cgt cag aat gca gga caa aca tgg aca gat        1568
Lys Trp Met Tyr Val Gly Arg Gln Asn Ala Gly Gln Thr Trp Thr Asp
        435                 440                 445 tta act ggt aat aac gga gcg tcc gtt aca att aat ggc gat gga tgg        1616
Leu Thr Gly Asn Asn Gly Ala Ser Val Thr Ile Asn Gly Asp Gly Trp
450                 455                 460 ggc gaa ttc ttt acg aat gga gga tct gta tcc gtg tac gtg aac caa        1664
```

```
Gly Glu Phe Phe Thr Asn Gly Gly Ser Val Ser Val Tyr Val Asn Gln
465                 470                 475                 480 taacaaaaag ccttgagaag ggattcctcc ctaactcaag gctttcttta tgtcgcttag    1724
cttaacgctt ctacgacttt gaagcttta                                      1753
```

<210> SEQ ID NO 4
<211> LENGTH: 480
<212> TYPE: PRT
<213> ORGANISM: Bacillus sp. KSM-K36

<400> SEQUENCE: 4

```
Asp Gly Leu Asn Gly Thr Met Met Gln Tyr Tyr Glu Trp His Leu Glu
                5                   10                  15

Asn Asp Gly Gln His Trp Asn Arg Leu His Asp Ala Glu Ala Leu
            20                  25                  30

Ser Asn Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Leu Gly Ala Asp Phe Thr
            100                 105                 110

Glu Ala Val Gln Ala Val Gln Val Asn Pro Ser Asn Arg Trp Gln Asp
        115                 120                 125

Ile Ser Gly Val Tyr Thr Ile Asp Ala Trp Thr Gly Phe Asp Phe Pro
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Leu Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Glu Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Ser Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Lys Gln Gly Gly Ser Tyr Asp Met
    290                 295                 300

Arg Asn Ile Leu Arg Gly Ser Leu Val Glu Ala His Pro Ile His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
```

-continued

```
                    340                 345                 350
Thr Arg Glu Gly Gly Tyr Pro Asn Val Phe Tyr Gly Asp Tyr Tyr Gly
                355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Ile Val Gly Trp Thr Arg Glu Gly Thr Ser Ser Arg
                    405                 410                 415

Pro Asn Ser Gly Leu Ala Thr Ile Met Ser Asn Gly Pro Gly Gly Ser
                420                 425                 430

Lys Trp Met Tyr Val Gly Gln Gln His Ala Gly Gln Thr Trp Thr Asp
            435                 440                 445

Leu Thr Gly Asn His Ala Ala Ser Val Thr Ile Asn Gly Asp Gly Trp
        450                 455                 460

Gly Glu Phe Phe Thr Asn Gly Gly Ser Val Ser Val Tyr Val Asn Gln
465                 470                 475                 480
```

<210> SEQ ID NO 5
<211> LENGTH: 1625
<212> TYPE: DNA
<213> ORGANISM: Bacillus sp.KSM-K36
<220> FEATURE:
<221> NAME/KEY: sig_peptide
<222> LOCATION: (40)..(102)
<221> NAME/KEY: mat_peptide
<222> LOCATION: (103)..(1542)
<221> NAME/KEY: CDS
<222> LOCATION: (40)..(1542)

<400> SEQUENCE: 5

```
atgatatatg taagcgttat cattaaaagg aggtatttg atg aaa aga tgg gta        54 gta gca atg ctg gca gtg tta ttt tta ttt cct tcg gta gta gtt gca      102 gat ggc ttg aat gga acg atg atg cag tat tat gag tgg cat cta gag      150
Asp Gly Leu Asn Gly Thr Met Met Gln Tyr Tyr Glu Trp His Leu Glu
1               5                   10                  15 aat gat ggg caa cac tgg aat cgg ttg cat gat gat gcc gaa gct tta      198
Asn Asp Gly Gln His Trp Asn Arg Leu His Asp Asp Ala Glu Ala Leu
                20                  25                  30 agt aat gcg ggt att aca gct att tgg ata ccc cca gcc tac aaa gga      246
Ser Asn Ala Gly Ile Thr Ala Ile Trp Ile Pro Pro Ala Tyr Lys Gly
            35                  40                  45 aat agt cag gct gat gtt ggg tat ggt gca tac gac ctt tat gat tta      294
Asn Ser Gln Ala Asp Val Gly Tyr Gly Ala Tyr Asp Leu Tyr Asp Leu
        50                  55                  60 ggg gag ttt aat caa aaa ggt acc gtt cga acg aaa tac ggg aca aag      342
Gly Glu Phe Asn Gln Lys Gly Thr Val Arg Thr Lys Tyr Gly Thr Lys
65                  70                  75                  80 gct cag ctt gag cga gct ata ggg tcc cta aag tcg aat gat atc aat      390
Ala Gln Leu Glu Arg Ala Ile Gly Ser Leu Lys Ser Asn Asp Ile Asn
                85                  90                  95 gtt tat ggg gat gtc gta atg aat cat aaa tta gga gct gat ttc acg      438
Val Tyr Gly Asp Val Val Met Asn His Lys Leu Gly Ala Asp Phe Thr
            100                 105                 110 gag gca gtg caa gct gtt caa gta aat cct tcg aac cgt tgg cag gat      486
Glu Ala Val Gln Ala Val Gln Val Asn Pro Ser Asn Arg Trp Gln Asp
        115                 120                 125 att tca ggt gtc tac acg att gat gca tgg acg gga ttt gac ttt cca      534
Ile Ser Gly Val Tyr Thr Ile Asp Ala Trp Thr Gly Phe Asp Phe Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 130 |     |     |     |     | 135 |     |     |     |     | 140 |     |     |     |      |
| ggg | cgc | aac | aat | gcc | tat | tcc | gat | ttt | aaa | tgg | aga | tgg | ttc | cat | ttt | 582  |
| Gly | Arg | Asn | Asn | Ala | Tyr | Ser | Asp | Phe | Lys | Trp | Arg | Trp | Phe | His | Phe |      |
| 145 |     |     |     |     | 150 |     |     |     |     | 155 |     |     |     |     | 160 |      |
| aat | ggc | gtt | gac | tgg | gat | caa | cgc | tat | caa | gaa | aac | cat | ctt | ttt | cgc | 630  |
| Asn | Gly | Val | Asp | Trp | Asp | Gln | Arg | Tyr | Gln | Glu | Asn | His | Leu | Phe | Arg |      |
|     |     |     |     | 165 |     |     |     |     | 170 |     |     |     |     | 175 |     |      |
| ttt | gca | aat | acg | aac | tgg | aac | tgg | cga | gtg | gat | gaa | gag | aat | ggt | aat | 678  |
| Phe | Ala | Asn | Thr | Asn | Trp | Asn | Trp | Arg | Val | Asp | Glu | Glu | Asn | Gly | Asn |      |
|     |     |     | 180 |     |     |     |     | 185 |     |     |     |     | 190 |     |     |      |
| tat | gac | tat | tta | tta | gga | tcg | aac | att | gac | ttt | agc | cac | cca | gag | gtt | 726  |
| Tyr | Asp | Tyr | Leu | Leu | Gly | Ser | Asn | Ile | Asp | Phe | Ser | His | Pro | Glu | Val |      |
|     |     | 195 |     |     |     |     | 200 |     |     |     |     | 205 |     |     |     |      |
| caa | gag | gaa | tta | aag | gat | tgg | ggg | agc | tgg | ttt | acg | gat | gag | cta | gat | 774  |
| Gln | Glu | Glu | Leu | Lys | Asp | Trp | Gly | Ser | Trp | Phe | Thr | Asp | Glu | Leu | Asp |      |
|     | 210 |     |     |     |     | 215 |     |     |     |     | 220 |     |     |     |     |      |
| tta | gat | ggg | tat | cga | ttg | gat | gct | att | aag | cat | att | cca | ttc | tgg | tat | 822  |
| Leu | Asp | Gly | Tyr | Arg | Leu | Asp | Ala | Ile | Lys | His | Ile | Pro | Phe | Trp | Tyr |      |
| 225 |     |     |     |     | 230 |     |     |     |     | 235 |     |     |     |     | 240 |      |
| acg | tca | gat | tgg | gtt | agg | cat | cag | cga | agt | gaa | gca | gac | caa | gat | tta | 870  |
| Thr | Ser | Asp | Trp | Val | Arg | His | Gln | Arg | Ser | Glu | Ala | Asp | Gln | Asp | Leu |      |
|     |     |     |     | 245 |     |     |     |     | 250 |     |     |     |     | 255 |     |      |
| ttt | gtc | gta | ggg | gag | tat | tgg | aag | gat | gac | gta | ggt | gct | ctc | gaa | ttt | 918  |
| Phe | Val | Val | Gly | Glu | Tyr | Trp | Lys | Asp | Asp | Val | Gly | Ala | Leu | Glu | Phe |      |
|     |     |     | 260 |     |     |     |     | 265 |     |     |     |     | 270 |     |     |      |
| tat | tta | gat | gaa | atg | aat | tgg | gag | atg | tct | cta | ttc | gat | gtt | ccg | ctc | 966  |
| Tyr | Leu | Asp | Glu | Met | Asn | Trp | Glu | Met | Ser | Leu | Phe | Asp | Val | Pro | Leu |      |
|     |     | 275 |     |     |     |     | 280 |     |     |     |     | 285 |     |     |     |      |
| aat | tat | aat | ttt | tac | cgg | gct | tca | aag | caa | ggc | gga | agc | tat | gat | atg | 1014 |
| Asn | Tyr | Asn | Phe | Tyr | Arg | Ala | Ser | Lys | Gln | Gly | Gly | Ser | Tyr | Asp | Met |      |
|     | 290 |     |     |     |     | 295 |     |     |     |     | 300 |     |     |     |     |      |
| cgt | aat | att | tta | cga | gga | tct | tta | gta | gaa | gca | cat | ccg | att | cat | gca | 1062 |
| Arg | Asn | Ile | Leu | Arg | Gly | Ser | Leu | Val | Glu | Ala | His | Pro | Ile | His | Ala |      |
| 305 |     |     |     |     | 310 |     |     |     |     | 315 |     |     |     |     | 320 |      |
| gtt | acg | ttt | gtt | gat | aat | cat | gat | act | cag | cca | gga | gag | tca | tta | gaa | 1110 |
| Val | Thr | Phe | Val | Asp | Asn | His | Asp | Thr | Gln | Pro | Gly | Glu | Ser | Leu | Glu |      |
|     |     |     |     | 325 |     |     |     |     | 330 |     |     |     |     | 335 |     |      |
| tca | tgg | gtc | gct | gat | tgg | ttt | aag | cca | ctt | gct | tat | gcg | aca | atc | ttg | 1158 |
| Ser | Trp | Val | Ala | Asp | Trp | Phe | Lys | Pro | Leu | Ala | Tyr | Ala | Thr | Ile | Leu |      |
|     |     |     | 340 |     |     |     |     | 345 |     |     |     |     | 350 |     |     |      |
| acg | cgt | gaa | ggt | ggt | tat | cca | aat | gta | ttt | tac | ggt | gac | tac | tat | ggg | 1206 |
| Thr | Arg | Glu | Gly | Gly | Tyr | Pro | Asn | Val | Phe | Tyr | Gly | Asp | Tyr | Tyr | Gly |      |
|     |     | 355 |     |     |     |     | 360 |     |     |     |     | 365 |     |     |     |      |
| att | cct | aac | gat | aac | att | tca | gct | aag | aag | gat | atg | att | gat | gag | ttg | 1254 |
| Ile | Pro | Asn | Asp | Asn | Ile | Ser | Ala | Lys | Lys | Asp | Met | Ile | Asp | Glu | Leu |      |
|     | 370 |     |     |     |     | 375 |     |     |     |     | 380 |     |     |     |     |      |
| ctt | gat | gca | cgt | caa | aat | tac | gca | tat | ggc | aca | caa | cat | gac | tat | ttt | 1302 |
| Leu | Asp | Ala | Arg | Gln | Asn | Tyr | Ala | Tyr | Gly | Thr | Gln | His | Asp | Tyr | Phe |      |
| 385 |     |     |     |     | 390 |     |     |     |     | 395 |     |     |     |     | 400 |      |
| gat | cat | tgg | gat | atc | gtt | gga | tgg | aca | aga | gaa | ggt | aca | tcc | tca | cgt | 1350 |
| Asp | His | Trp | Asp | Ile | Val | Gly | Trp | Thr | Arg | Glu | Gly | Thr | Ser | Ser | Arg |      |
|     |     |     |     | 405 |     |     |     |     | 410 |     |     |     |     | 415 |     |      |
| cct | aat | tcg | ggt | ctt | gct | act | att | atg | tcc | aat | ggt | cct | gga | gga | tca | 1398 |
| Pro | Asn | Ser | Gly | Leu | Ala | Thr | Ile | Met | Ser | Asn | Gly | Pro | Gly | Gly | Ser |      |
|     |     |     | 420 |     |     |     |     | 425 |     |     |     |     | 430 |     |     |      |
| aaa | tgg | atg | tac | gta | gga | cag | caa | cat | gca | gga | caa | acg | tgg | aca | gat | 1446 |
| Lys | Trp | Met | Tyr | Val | Gly | Gln | Gln | His | Ala | Gly | Gln | Thr | Trp | Thr | Asp |      |
|     |     | 435 |     |     |     |     | 440 |     |     |     |     | 445 |     |     |     |      |
| tta | act | ggc | aat | cac | gcg | gcg | tcg | gtt | acg | att | aat | ggt | gat | ggc | tgg | 1494 |

```
Leu Thr Gly Asn His Ala Ala Ser Val Thr Ile Asn Gly Asp Gly Trp
    450                 455                 460 ggc gaa ttc ttt aca aat gga gga tct gta tcc gtg tat gtg aac caa    1542
Gly Glu Phe Phe Thr Asn Gly Gly Ser Val Ser Val Tyr Val Asn Gln
465                 470                 475                 480 taataaaaag ccttgagaag ggattcctcc ctaactcaag gctttcttta tgtcgtttag   1602
ctcaacgctt ctacgaagct tta                                          1625

<210> SEQ ID NO 6
<211> LENGTH: 30
<212> TYPE: DNA
<213> ORGANISM: Artificial Sequence
<220> FEATURE:
<223> OTHER INFORMATION: PCR Primer

<400> SEQUENCE: 6
atgatgcagt attttgagtg gcatttggaa                                      30

<210> SEQ ID NO 7
<211> LENGTH: 33
<212> TYPE: DNA
<213> ORGANISM: Artificial Sequence
<220> FEATURE:
<223> OTHER INFORMATION: PCR Primer

<400> SEQUENCE: 7
tatgagtggc atttgccaaa cgacgggcag cat                                  33

<210> SEQ ID NO 8
<211> LENGTH: 33
<212> TYPE: DNA
<213> ORGANISM: Artificial Sequence
<220> FEATURE:
<223> OTHER INFORMATION: PCR Primer

<400> SEQUENCE: 8
ccagcctaca aaggtagtag tcaggcggat gtt                                  33

<210> SEQ ID NO 9
<211> LENGTH: 21
<212> TYPE: DNA
<213> ORGANISM: Artificial Sequence
<220> FEATURE:
<223> OTHER INFORMATION: PCR Primer

<400> SEQUENCE: 9
gcacagcttc aacgagctat t                                               21

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
tttcgacttt ccagggcgta a                                               21

<210> SEQ ID NO 11
<211> LENGTH: 33
<212> TYPE: DNA
<213> ORGANISM: Artificial Sequence
<220> FEATURE:
<223> OTHER INFORMATION: PCR Primer
```

-continued

<400> SEQUENCE: 11
catattttcc gctttcaaaa tacgaactgg aac                                    33

<210> SEQ ID NO 12
<211> LENGTH: 33
<212> TYPE: DNA
<213> ORGANISM: Artificial Sequence
<220> FEATURE:
<223> OTHER INFORMATION: PCR Primer

<400> SEQUENCE: 12
aactggcgag tggatgatga gaacggtaat tat                                    33

<210> SEQ ID NO 13
<211> LENGTH: 25
<212> TYPE: DNA
<213> ORGANISM: Artificial Sequence
<220> FEATURE:
<223> OTHER INFORMATION: PCR Primer

<400> SEQUENCE: 13
tggatgaaga gttcggtaat tatga                                             25

<210> SEQ ID NO 14
<211> LENGTH: 33
<212> TYPE: DNA
<213> ORGANISM: Artificial Sequence
<220> FEATURE:
<223> OTHER INFORMATION: PCR Primer

<400> SEQUENCE: 14
aatatcgact ttagtcgtcc agaagtacaa gat                                    33

<210> SEQ ID NO 15
<211> LENGTH: 33
<212> TYPE: DNA
<213> ORGANISM: Artificial Sequence
<220> FEATURE:
<223> OTHER INFORMATION: PCR Primer

<400> SEQUENCE: 15
agtcatccag aggtcgtaga tgagttgaag gat                                    33

<210> SEQ ID NO 16
<211> LENGTH: 33
<212> TYPE: DNA
<213> ORGANISM: Artificial Sequence
<220> FEATURE:
<223> OTHER INFORMATION: PCR Primer

<400> SEQUENCE: 16
gttgactggg atgagcgcaa acaagaaaat cat                                    33

<210> SEQ ID NO 17
<211> LENGTH: 34
<212> TYPE: DNA
<213> ORGANISM: Artificial Sequence
<220> FEATURE:
<223> OTHER INFORMATION: PCR Primer

<400> SEQUENCE: 17
atttgccaaa tgacgggcag cattggaatc ggtt                                   34

<210> SEQ ID NO 18
<211> LENGTH: 34

```
<212> TYPE: DNA
<213> ORGANISM: Artificial Sequence
<220> FEATURE:
<223> OTHER INFORMATION: PCR Primer

<400> SEQUENCE: 18
aaccgattcc aatgctgccc gtcatttggc aaat                          34

<210> SEQ ID NO 19
<211> LENGTH: 40
<212> TYPE: DNA
<213> ORGANISM: Artificial Sequence
<220> FEATURE:
<223> OTHER INFORMATION: PCR Primer

<400> SEQUENCE: 19
gggtcgacca gcacaagccg atggattgaa cggtacgatg                    40

<210> SEQ ID NO 20
<211> LENGTH: 29
<212> TYPE: DNA
<213> ORGANISM: Artificial Sequence
<220> FEATURE:
<223> OTHER INFORMATION: PCR Primer

<400> SEQUENCE: 20
taaagctttt gttattggtt cacgtacac                                29

<210> SEQ ID NO 21
<211> LENGTH: 30
<212> TYPE: DNA
<213> ORGANISM: Artificial Sequence
<220> FEATURE:
<223> OTHER INFORMATION: PCR Primer

<400> SEQUENCE: 21
gagtcgacca gcacaagccc atcataatgg                               30

<210> SEQ ID NO 22
<211> LENGTH: 21
<212> TYPE: DNA
<213> ORGANISM: Artificial Sequence
<220> FEATURE:
<223> OTHER INFORMATION: PCR Primer

<400> SEQUENCE: 22
taaagcttca atttatattg g                                        21

<210> SEQ ID NO 23
<211> LENGTH: 27
<212> TYPE: DNA
<213> ORGANISM: Artificial Sequence
<220> FEATURE:
<223> OTHER INFORMATION: PCR Primer

<400> SEQUENCE: 23
ccagatctac ttaccatttt agagtca                                  27
```